United States Patent
Eckles

(10) Patent No.: US 6,317,212 B1
(45) Date of Patent: Nov. 13, 2001

(54) GAS ANALYZER

(75) Inventor: Robert D. Eckles, Malcolm, NE (US)

(73) Assignee: Li-Cor, Inc., Lincoln, NE (US)

( * ) Notice: Subject to any disclaimer, the term of this patent is extended or adjusted under 35 U.S.C. 154(b) by 0 days.

(21) Appl. No.: 09/397,903

(22) Filed: Sep. 17, 1999

(51) Int. Cl.$^7$ ................................................ G01N 21/61
(52) U.S. Cl. ....................................... 356/437; 250/338.5
(58) Field of Search .................................. 356/437, 438, 356/439; 250/338.5

(56) References Cited

U.S. PATENT DOCUMENTS

| | | | |
|---|---|---|---|
| 3,696,247 | * 10/1972 | McIntosh et al. | 250/339.07 |
| 4,013,260 | * 3/1977 | McClatchie et al. | 250/343 |

(List continued on next page.)

OTHER PUBLICATIONS

Jones et al., A Fast Response Atmospheric $CO_2$ Sensor for Eddy Correlation Flux Measurements, *Atmospheric Environment*, vol. 12, pp. 845–851, Pergamon Press Ltd. 1978.
Bingham et al., Development of a Miniature, Rapid––Response Carbon Dioxide Sensor, Progress Report from the NSF Ecosystem Program, The National Science Foundation, (Project DEB 77–16327), Mar. 20, 1978.
Brach et al., Open Path $CO_2$ Analyser, *The Institute of Physics*, vol. 6, pp. 1415–1419, 1981.
Altmann et al., Two–Mirrow Multipass Absorption Cell, *Applied Optics*, vol. 20, No. 6, pp. 995–999, Mar. 15, 1981.
Heikinheimo et al., An Open Path, Fast Response IR Spectrometer for Simultaneous Detection of $CO_2$ and Water Vapor Fluctuations, *Journal of Atmospheric and Oceanic Technology*, vol.6, pp. 624–636, Aug. 1989.
Bingham et al., Fast–Response Sensors for Eddy Covariance Measurements of $CO_2$ and Other Middle Infrared Absorbing Gases, Private Communication, not dated.
Bingham, Gail E., A Miniature Rapid Response Sensor for Atmospheric Concentrations of Carbon Dioxide, Private Communication, not dated.
Ohtaki, Eiji and Matsui, Tetuji, Infrared Device for Simultaneous Measurement of Fluctuations of Atmospheric Carbon Dioxide and Water Vapor, *Boundary–Layer Meterology*24 (1982) 109–119.
Auble, David L. and Meyers, Tilden P., An Open Path, Fast Response Infrared Absorption Gas Analyzer for $H_2O$ and $CO_2$ ,Boundary–Layer Meterology 59: 243–256, 1992.
Internet Web page entitled Infrared Gas Analyzer, www.atdd.noaa.gov/irga/irga.htm, Jul. 6, 1999.
Internet Web page entitled Advance Optima Infrared Analyzer Module Uras 14, www.hub.de/world/analyse/en/optima/p_aui_01.htm, Jul. 9, 1999.
Internet Web page entitled Dynamax Inc.—ADC 2250 Series, www.dynamax.com/adc.htm, Jul.9, 1999.
Internet Web page entitled Infra–Red Gas Analysis Systems CIRAS–1, CIRAS–2 SC & DC, www.ppsystems.com/gas2.html, Jul. 9, 1999.

(List continued on next page.)

*Primary Examiner*—Richard A. Rosenberger
(74) *Attorney, Agent, or Firm*—Brinks Hofer Gilson & Lione; Jason C. White

(57) ABSTRACT

The present gas analyzer allows for the effective measurement of the concentration of one or more gases or vapors within a sample. The gas analyzer utilizes a plurality of reference filters that are located between the source and the sample region to enhance the measurements associated with the sample filters. The gas analyzer also utilizes a gas channel to facilitate the circulation of scrubbed gas between two separate housing sections.

14 Claims, 5 Drawing Sheets

U.S. PATENT DOCUMENTS

| | | | |
|---|---|---|---|
| 4,567,366 | * | 1/1986 | Shinohara .............................. 250/339 |
| 4,569,589 | * | 2/1986 | Neufeld ................................ 356/416 |
| 5,340,987 | | 8/1994 | Eckles et al. . |

OTHER PUBLICATIONS

Internet Web page entitled Gas Analysis Ultramat 6, www3.ad.siemens.de/ca01cache/en_3000133_b_tab0_IE4.htm, Jul. 9, 1999.

Internet Web page entitled Gas Analysis Ultramat 23, www3.ad.siemens.de/ca/01cache/en_3000134_b_tab0_IE4.htm, Jul. 9, 1999.

Internet Web page entitled Gas Analysis Ultramat 5F–Ex u. 5F–2R–Ex, www3.ad.siemens.de/ca01cache/en_3000137_b_tab0_IE4.htm, Jul. 9, 1999.

Internet Web page entitled Gas Analysis Ultramat/Oxymat 6, www3.ad.siemens.de/ca01cache/en_3000154_b_tab0_IE4.htm, Jul. 9, 1999.

* cited by examiner

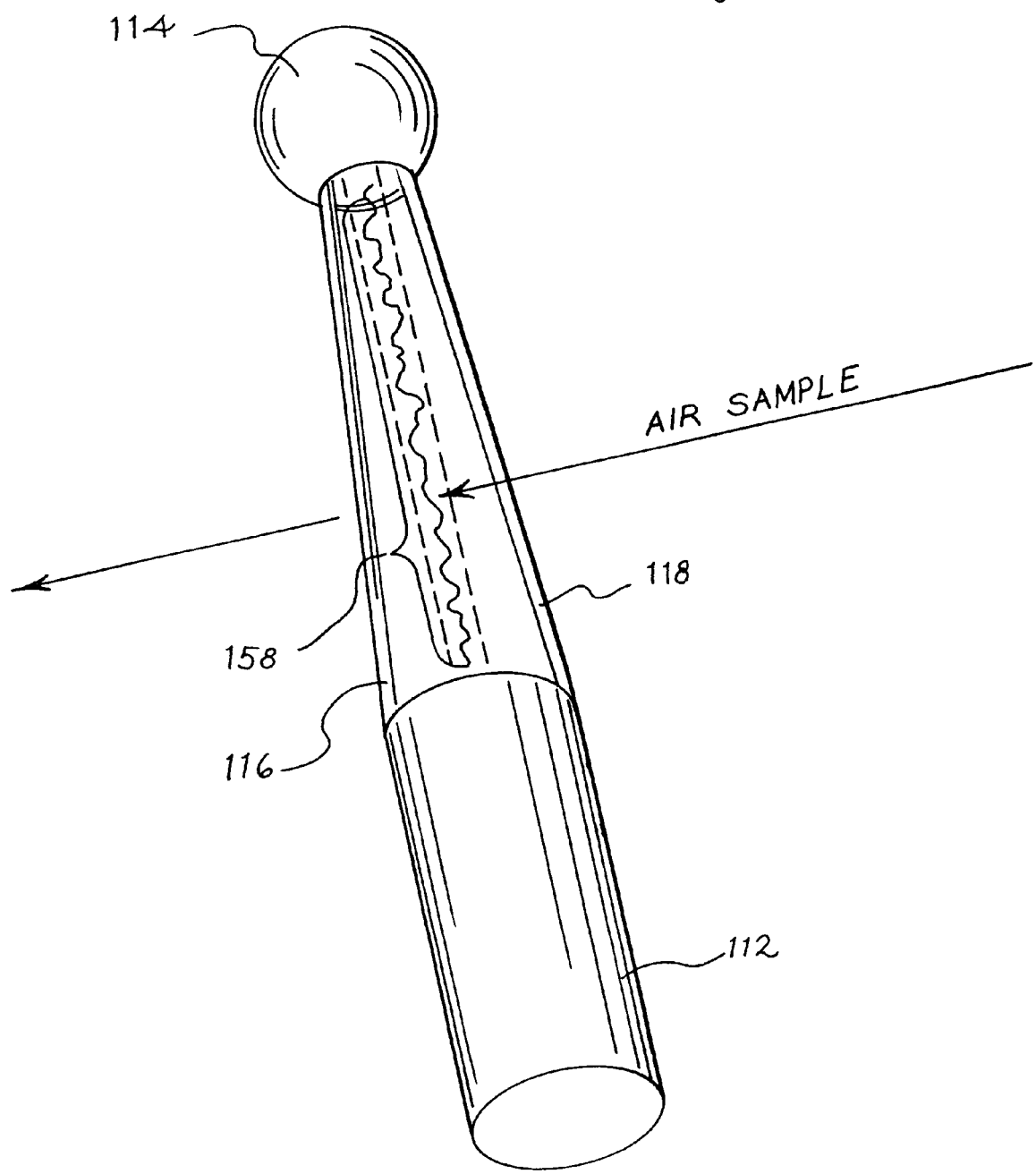

GAS ANALYZER

BACKGROUND

The present invention relates generally to measuring the concentration of gases and/or vapor in a sample and more particularly to measuring the concentration of carbon dioxide and water vapor in the air.

One type of gas analyzer utilizes a light source that projects a beam of light through a sample and a detector to detect the light after passing through the sample. These gas analyzers typically use a combination of sample filters and a single reference filter to analyze certain wave lengths of light. The concentrations of gases in the sample can be determined by examining the degree to which the certain wave lengths of light are absorbed by the sample. However, by using a single reference filter in conjunction with two or more sample filters, the accuracy of the measurements associated with the two sample filters may be decreased. In this analyzer, the filters are typically placed between the sample and the detector. However, this placement of the filters in relation to the source may render the analyzer more susceptible to drift, artifacts, and the like, which may reduce the accuracy of the analyzer.

Further, to measure the concentrations of gases in air, one type of gas analyzer utilizes an open air measuring chamber. This type of analyzer typically includes a source that produces light, a detector to receive the light, an a pair of mirrors that reflect the light to direct it from the source to the detector. When these mirrors are used in an open air measuring chamber, they are exposed to the environment and are subject to contamination that can effect the accuracy of the analyzer. Therefore, an analyzer that overcomes these deficiencies is needed.

BRIEF DESCRIPTION OF THE DRAWINGS

FIG. 6 is perspective view of the gas analyzer of FIG. 3.

DETAILED DESCRIPTION OF THE PRESENTLY PREFERRED EMBODIMENTS

By way of introduction, the preferred embodiments described below include a gas analyzer for determining the concentrations of gases and vapors within a sample. In one embodiment, the gas analyzer utilizes a light source and a detector to measure the absorption of different wavelengths of light by the sample. The light source generates a beam of light that is used to measure the light absorbed by the sample. This light beam also serves a reference. A plurality of filters, including at least one sample filter and at least two reference filters, are located between the source and the sample to filter the light from the source. By using a plurality of reference filters located between the source and the sample, the concentration of gas or vapor within the sample can be accuracy determined.

For example, to measure the concentration of $CO_2$ and $H_2O$ in an air sample, light from the source is passed through the first sample filter that is designed to let certain wavelengths of light, which correspond to $CO_2$, pass. After passing through this filter, the remaining wave lengths of light pass through the sample and are received by the detector. The sample filter is then replaced by a first reference so that light from the source passes through the first reference filter. The first reference filter lets wavelengths of light, which correspond to $CO_2$, and are near the first sample filter's wavelength, pass. After passing through this filter, the remaining light passes through the sample and is received by the detector. The concentration of $CO_2$ can the be determined by calculating the difference in the absorption of the two wavelengths of light. This same process can be repeated, using a second reference filter and a second sample filter, to measure the concentration $H_2O$. By using two reference filters, the concentration of the gases can be more accurately determined.

In another embodiment, a gas analyzer comprises two housing sections that are spatially separated by an open air measuring region. Gases that are to be analyzed can flow freely between the housing sections in the open air measuring region. The two housing sections are joined by gas channels that enable gas to circulate between the housing sections. Because the gas can circulate between the housing sections, the gas within both housing sections can be scrubbed by a single scrubber, which removes one or more gases from within the housing. This can reduce the number of components required to scrub the gas contained within the different portions of the analyzer.

Figure 1:
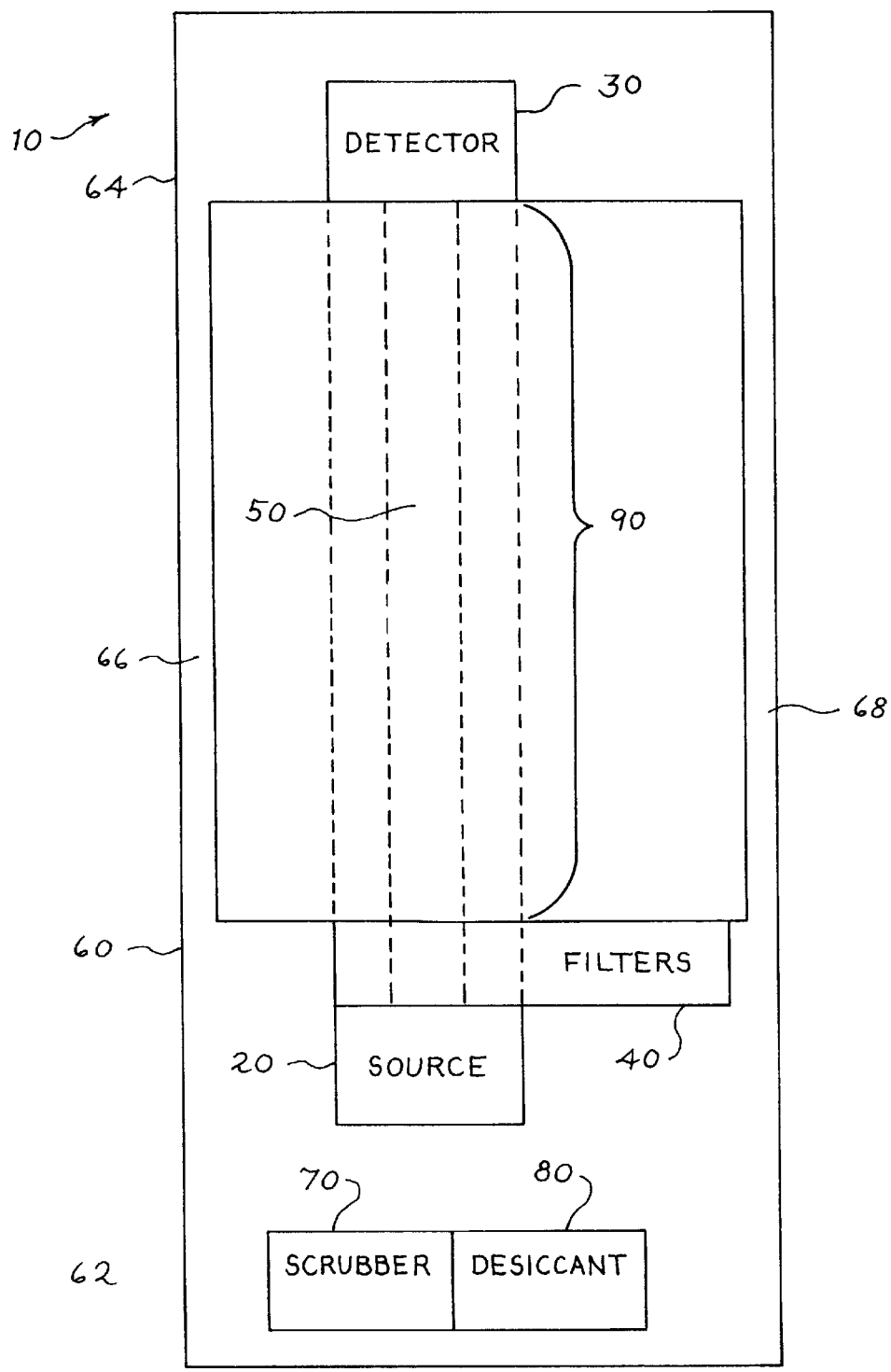
FIG. 1 is a block diagram of a gas analyzer of a preferred embodiment.

By way of example, FIG. 1 depicts a gas analyzer 10 of a preferred embodiment. The gas analyzer 10 comprises a source 20, a detector 30 optically coupled with the source 20, and a plurality of filters 40 intermittently disposed within an optical path 50 between the source 20 and the detector 30. The term "coupled with," as used herein, means directly coupled with or indirectly coupled with through one or more components. The source 20 preferably comprises a light source such as a lamp. The source 20 preferably comprises an infrared light source but can also comprise a near infrared light source, an ultraviolet light source, or any other suitable light source.

The detector 30 preferably comprises a light detector that is responsive to the form of light produced by the source 20. The detector 30 preferably converts the light it receives into a an electrical voltage, which can be used to determine the absorption of the light in the sample. The detector 30 preferably has a high signal-to-noise ratio and a high sensitivity.

Figure 2:
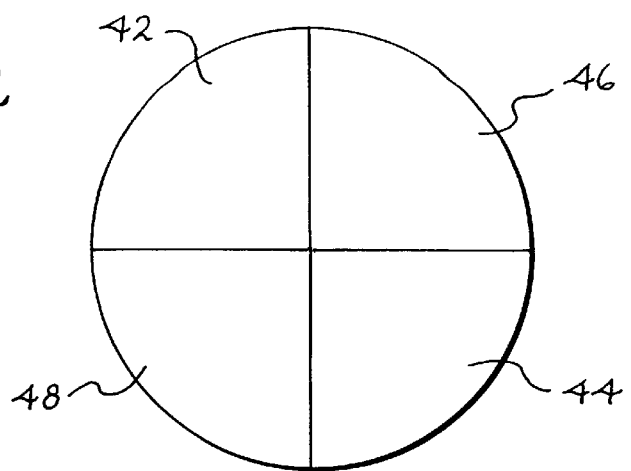
FIG. 2 is a block diagram of a plurality of filters.

The plurality of filters 40 preferably comprises at least one sample filter 42 and at least two reference filters 46, 48 as depicted in FIG. 2. The filters 42, 46, 48 preferably comprise interference filters but can also comprise absorption filters or other such filters. The filters 42, 46, 48 serve as a band pass light filters that allow light waves between a certain range of wave lengths to pass while preventing other wavelengths of light from passing. The band of the sample filter 42 is preferably centered around the wavelength of the particular gas or vapor this is to be analyzed by the gas analyzer 10. The band of the first reference filter 46 is preferably centered around the wavelength that is near the wavelength of the particular gas or vapor this is sought to be measured, is not in the band of the other filters, and does not equal the wavelength of another gas or vapor. The second reference filter 48 can be located near the same reference filter as the first reference filter 46, particularly when only one sample filter is utilized or can be located near the second reference filter 48 when two reference filters are utilized. In an alternative embodiment the plurality of filters 40 can comprise a second sample filter 44 that corresponds to second gas or vapor that is to be measured.

The plurality of filters 40 can be disposed on a support member as described below in reference to FIGS. 4 and 5 or can be coupled with one another. The plurality of filters 40 are preferably located between the source 20 and an optical path measuring region 90 (FIG. 1). By orienting the plurality of filters 40 in this fashion, drift and artifacts associated with the analyzer 10 can be eliminated. Alternatively, the plurality of filters 40 can be located between the optical path measuring region 90 and the detector 30. The optical path measuring region 90 comprises a portion of the optical path 50 in which the sample that is to be analyzed is located. The optical path measuring region 90 preferably comprises an open air measuring region wherein air can flow freely through the optical path 50.

In an alternative embodiment, the plurality of filters 40 can be utilized in conjunction with a gas analyzer that utilizes a closed air measuring chamber. In addition, the plurality of filters 40 are depicted in a gas analyzer having a straight optical path 50. In this configuration, a limited number of components are exposed to the sample gas and the analyzer is less susceptible to contamination and can provide reliable measurements of the sample. In an alternative embodiment, the source 20 and the detector 30 can be configured to form a bended optical path and the plurality of filters can be used in conjunction with the bended optical path gas analyzer.

The gas analyzer 10 preferably further comprises a housing 60, a scrubber 70 disposed within the housing 60, and a desiccant 80 disposed within the housing 60. The housing 60 preferably comprises a first housing section 62, a second housing section 64, and a gas channel 66 coupling the first housing section 62 with the second housing section 64. The first housing section 62, second housing section 64, and gas channel 66 are preferably constructed from a material such as aluminum that readily dissipates heat. The material is preferably coated with a material that does not affect the ability of the scrubber 70 or desiccant 80 to remove certain gases/vapors. One suitable coating is irradiated nickel. Alternatively, the first housing section 62, second housing section 64, and gas channel 66 can be constructed from any material that effectively contain and support the element described herein. In an alternative embodiment, the housing 60 can comprise a plurality of gas channels 66, 68 for coupling the first housing section 62 with the second housing section 64.

The scrubber 70 preferably comprises a quantity of gas absorbing material located within the housing. For example, the scrubber 70 can comprise a quantity of soda lime that absorbs $CO_2$. Alternatively, the scrubber 70 can comprise any type of absorbing material with the type of material selected to absorb the gas or vapor that is to be analyzed by the gas analyzer 10. The desiccant 80 preferably comprises quantity of vapor absorbing material located within the housing. For example, the desiccant 80 can comprise a quantity of drierite, silicagel, or magnesium perchlorate that absorbs $H_2O$. In an alternative embodiment, the gas analyzer 10 can comprise a plurality of scrubbers that are each capable of removing different gases or vapors from the gas within the housing 60. The plurality of scrubbers can be used in conjunction with or in place of the desiccant 80.

While the gas channel 66 is depicted in a gas analyzer having a straight optical path 50, the first housing section 62 and the second housing section 64 can be configured to form a bended optical path, and the gas channel 66 can be used in conjunction with the bended optical path gas analyzer. Further, while the gas channel 60 is depicted in a gas analyzer that incorporates an open air optical path measuring region, the gas channel 66 can be utilized in conjunction with a gas analyzer that utilizes a closed air measuring chamber.

Figure 3:
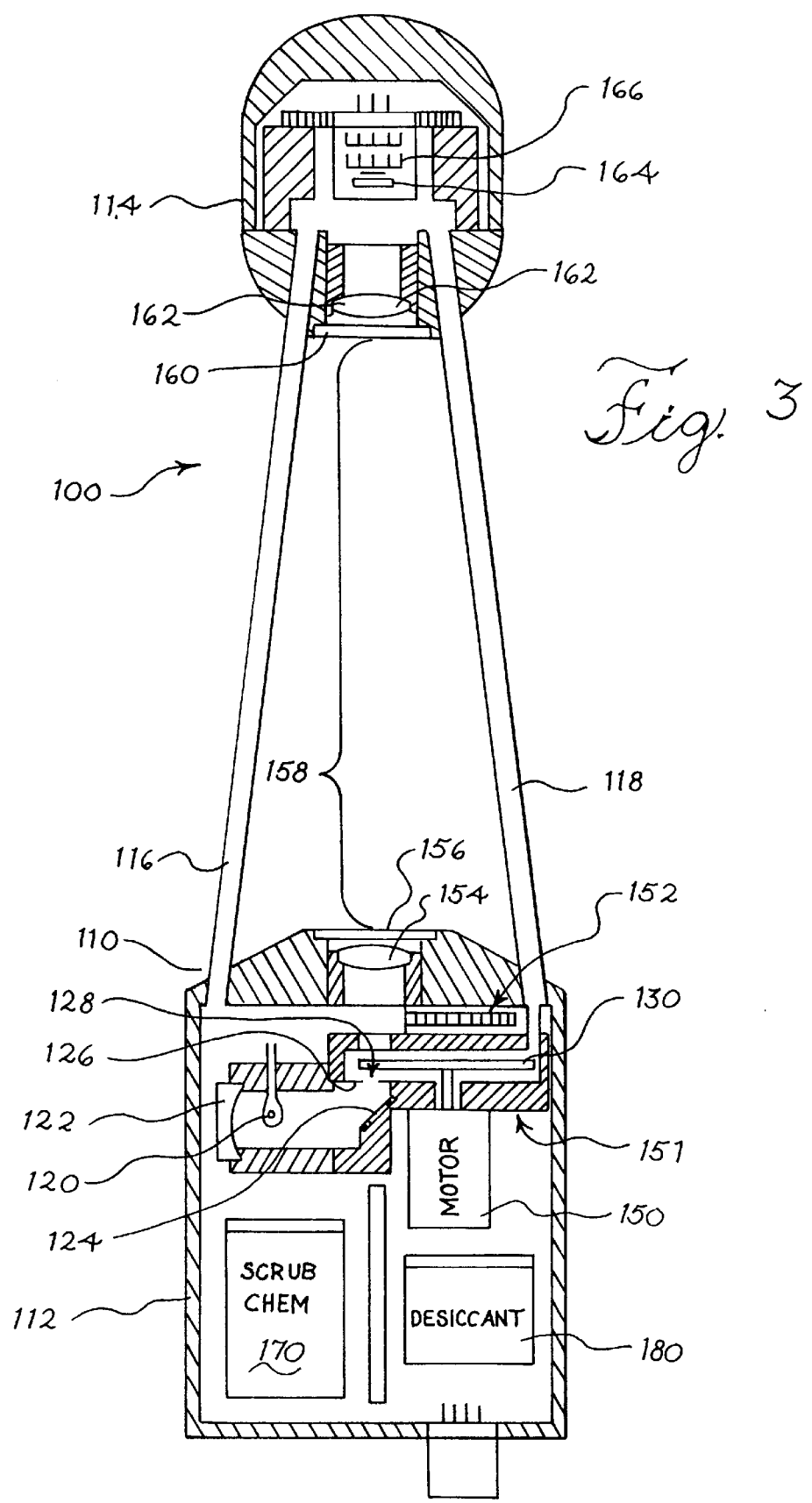
FIG. 3 is a sectional view of a first preferred embodiment of the gas analyzer of FIG. 1.
Figure 7:
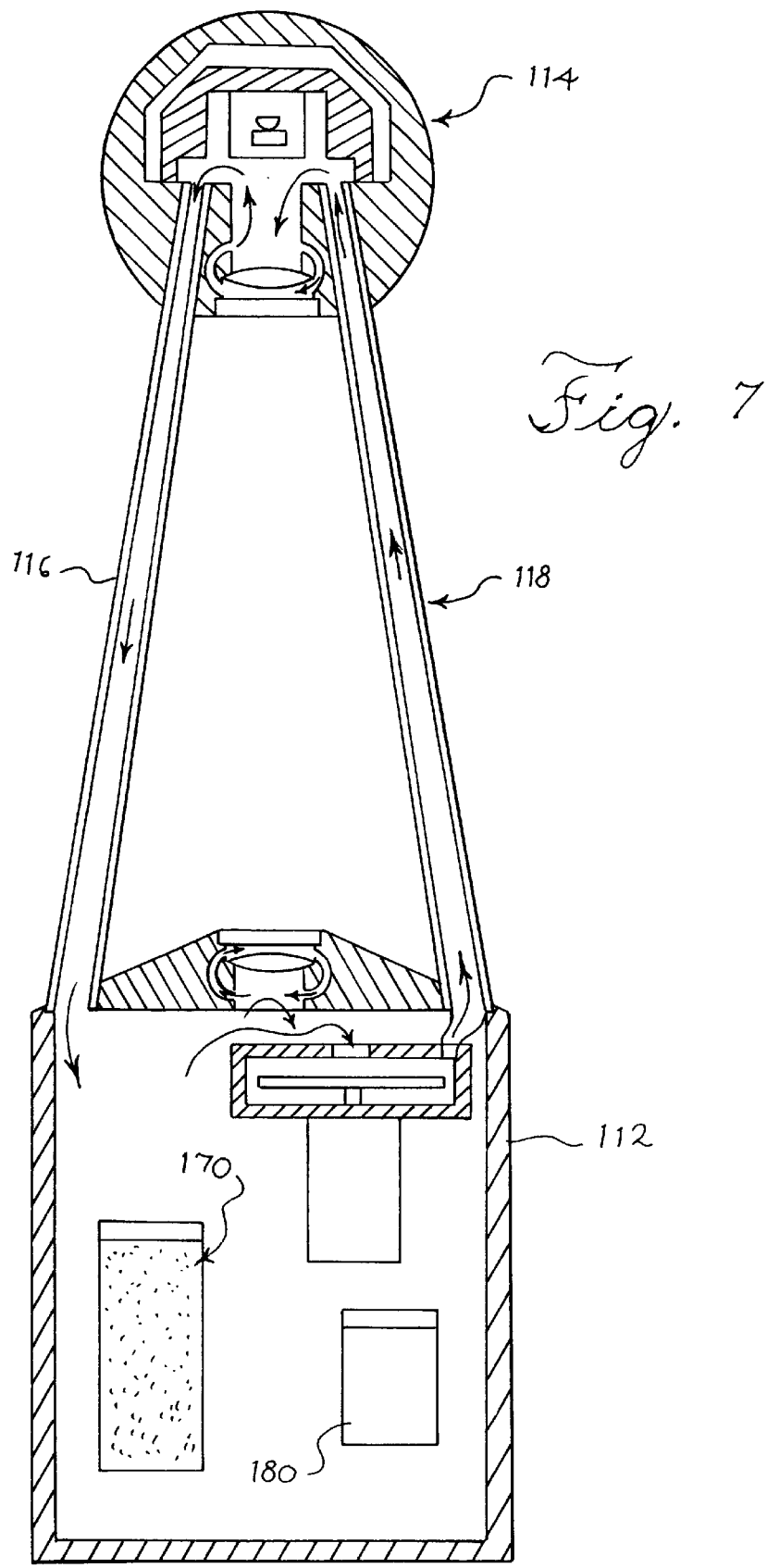
FIG. 7 is a sectional view of a first preferred embodiment of the gas analyzer of FIG. 1.

By way of further example, FIG. 3 depicts a preferred embodiment of the gas analyzer 10 described above. The gas analyzer 100 comprises a housing 110. The housing 110 preferably comprises a first housing section 112, a second housing section 114, and a plurality of gas channels 116, 118 coupling the first housing section 112 with the second housing section 114. The housing 110 is preferably constructed from materials are rugged, resist damage, and dissipate heat as described above. In a preferred embodiment, the housing 110 is constructed from aluminum that includes an anodized coating such as irradiated nickel. The housing 110 is preferably formed with round edges that do not interrupt air flow of sample gases into the open air optical path measuring region 158 as depicted in FIG. 6. Alternatively, the housing 110 can be formed from any suitable material and can be of any suitable shape and size. As noted above, the gas channels 116, 118 enable scrubbed gas to flow between the first housing section 112 and the second housing section 114 as depicted in FIG. 7 wherein arrows are included to show one possible gas circulation pattern. The scrubbed gases can also flow in and between the components contained within the housing sections 112, 114.

The gas analyzer 100 further comprises an infrared source 120, a focus mirror 122, a directing mirror 124, an optical stop 126, a filter member 130, a first focus lens 154, and a first window 156 disposed within the first housing section 112. The infrared source 120 preferably comprises an infrared lamp having a filament. One suitable infrared lamp is Gilway Technical Lamp's model 4115 infrared lamp.

The focus mirror 122 preferably comprises a concave mirror with a 0.5 inch radius internal curvature. The focus mirror 122 is preferably round is shape with a 0.5 inch diameter and preferably has a protective overcoat consisting of evaporated gold with silicon monoxide. Alternatively, the focus mirror 122 can comprise a mirror or other reflective material of any size and shape. The focus mirror 122 focuses the light from the infrared light source 120 to effectively increase the image size of the filament from the infrared light source 120 so that the image size of the filament uniformly fills the opening in the optical stop 126.

The directing mirror 124 is preferably a flat rectangular mirror having a length of 0.375 inches and a width of 0.25 inches and preferably has a protective overcoat consisting of evaporated gold with silicon monoxide. Alternatively, the directing mirror 124 can comprise a mirror or other reflective material of any size and shape. The directing mirror 124 directs the light from the focus mirror 122 towards the filter member 130 and enables the components the produce the light that is supplied to the optical stop to be fit within a smaller physical space that would normally be required.

The optical stop 126 preferably comprises a stainless steel disc including an opening 128 formed therein. The optical stop 126 preferably has a thickness of 0.003 inches, an inner diameter of 0.07 inches, and an outer diameter of 0.4 inches. Alternatively, the optical stop 126 can comprise any material that prevents light from passing through the material, can be of any size and shape, and can include an opening of any size or shape. The optical stop 126 serves as an aperture that limits the diameter of the light that is projected onto the first focus lens 154 by restricting light from passing through any portion other than the opening 128. The size of the opening 128 is preferably selected so that the diameter of the light that produced by the first focus lens 154 matches the diameter of the second focusing lens 162.

Figure 4:
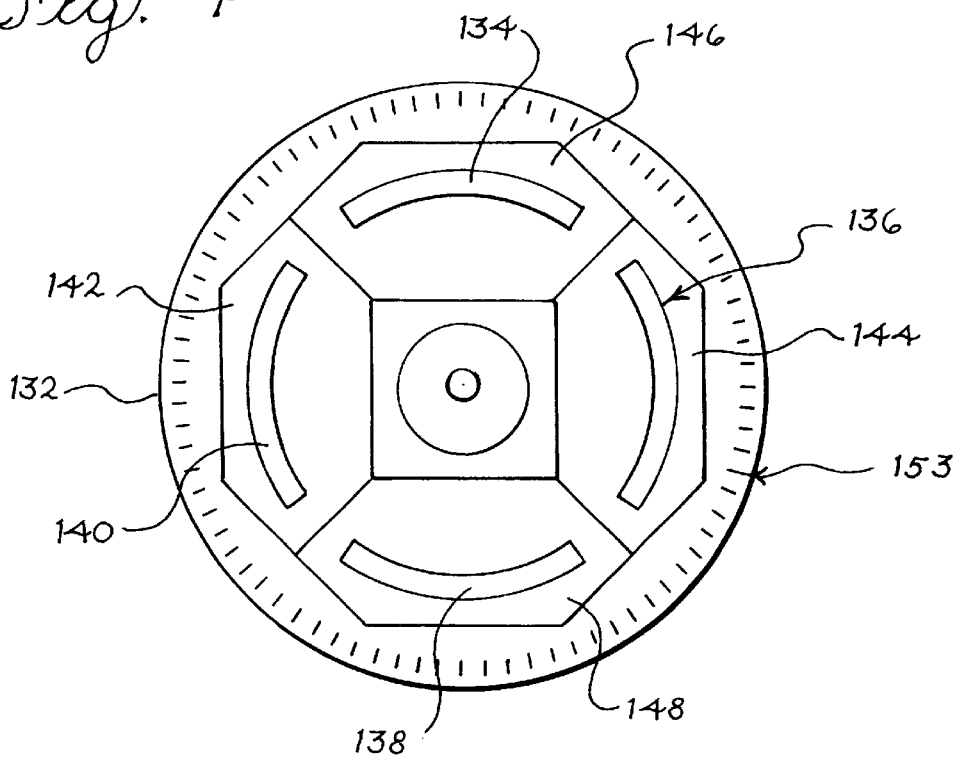
FIG. 4 is a top view of a filter member of a preferred embodiment.
Figure 5:
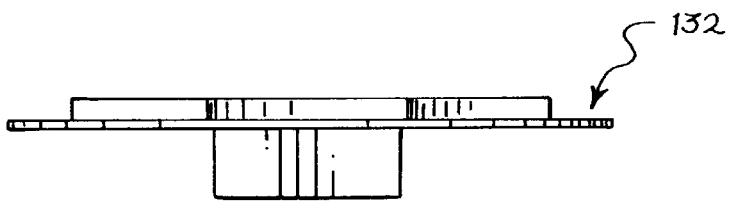
FIG. 5 is a side view of the filter member of FIG. 4.

The filter member 130 preferably comprises a support member 132 having a plurality of apertures 134, 136, 138, 140 formed therein, a plurality of sample filters 142, 144 coupled with the support member 132, and a plurality of reference filters 146, 148 coupled with the support member 132 as depicted in FIGS. 4 and 5. The support member 132 preferably comprises a stainless steel wheel 1.0 inches in diameter and 0.005 inches thick. Alternatively, the support member can comprise any type of material of any shape or size. The apertures 134, 136, 138, 140 preferably comprise crescent shaped openings formed within support member 132. Alternatively, the apertures 134, 136, 138, 140 can be of any size and shape. The apertures 134, 136, 138, 140 allow light to pass through the filters as described below.

The support member 132 is preferably moveably oriented such that when moved, one of the filters 142, 144, 146, 148 is disposed within the optical path. The support member is preferably rotatably disposed near the optical path. A motor 150 is preferably coupled with the support member 132 to facilitate the rotation of the support member 132. Other suitable mechanisms and arrangements for moving the support member 132 may alternatively be used. The motor 150 preferably comprises a brushless DC motor such as Micro-Mo's model 1628T024B. Alternatively, the motor 150 can comprise any suitable motor for moving the support member 132.

The support member 132 is preferably disposed within a filter housing 151. The filter housing 151 is preferably coupled with a heating/cooling element 152. The heating/cooling element 152 preferably comprises a thermoelectric heat pump such as the Melcor model CP 8-63-06L-1. The heating/cooling element 152 measures the temperature of the filter housing 151 and maintains the temperature within a predetermined range by heating or cooling the filter housing 152. By maintaining the temperature of the filter housing 152 within a predetermined range, the filters 142, 144, 146, 148 are also maintained within that range to minimize drift and operate at maximum efficiency.

The support member 132 preferably further comprises a plurality of timing slots 153 (FIG. 4) formed around the periphery of the support member. The timing slots 153 can be used in conjunction with a light emitting diode and a photo detector to determine the position of the support element 132 and, thus, the position of the filters 142, 144, 146, 148. Alternatively, any other suitable systems for determining the position (rotational or otherwise) of the filters 142, 144, 146, 148 with respect to the light can be utilized.

The sample filters 142, 144 preferably comprise band pass light filters as described above. The sample filters 142, 144 are preferably 0.25 inches by 0.375 inches and are coupled with the support member such that each of the sample filters 142, 144 covers one of the apertures 134, 136, 138, 140. The reference filters 146, 148 preferably comprise band pass light filters as described above. The reference filters 146, 148 are preferably 0.25 inches by 0.375 inches and are coupled with the support member such that each of the reference filters 146, 148 covers one of the apertures 134, 136, 138, 140.

The first focus lens 154 preferably comprises a bi-convex lens with the curvatures being based on a 0.5 inch radius and having an effective focal length of 0.75 inches. The first focus lens 154 is preferably made from calcium fluoride. The first focus lens 154 is preferably located between the filters and the optical path measuring region 158 and serves to increase the diameter of the light that is passed through the optical path measuring region 158.

The first window 156 preferably comprises a 0.02 inch thick disk made from synthetic sapphire and having a diameter of 0.75 inches. Alternatively, the first window 156 can comprise any material that enables light to pass through and can be or any size or shape. The first window 156 is preferably located between the first focus lens 154 and optical path measuring region 158 and serves to protect the first focus lens 154 by preventing it from being exposed to the gas within the optical path measuring region 158.

The gas analyzer 100 further comprises an optical path measuring region 158 and a second window 160, a second focusing lens 162, a solar filter 164, and a detector 166 disposed within the second housing section 114. The optical path measuring region 158 preferably comprises a portion of the optical path between the source 120 and the detector 166. The optical path measuring region 158 comprises the portion of the optical path in which the sample that is to be analyzed is located and is preferably an open air path as described above.

The second window 160 preferably comprises preferably comprises a 0.02 inch thick disk made from synthetic sapphire and having a diameter of 0.75 inches. Alternatively, the second window 160 can comprise any material that enables light to pass through and can be or any size or shape. The second window 160 is preferably located between the optical path measuring region 158 and the second focus lens 162 and serves to protect the second focus lens 162 by preventing it from being exposed to the gas within the optical path measuring region 158.

The second focus lens 162 preferably comprises a bi-convex lens with the curvatures being based on a 0.5 inch radius and having an effective focal length of 0.75 inches. The second focus lens 162 is preferably made from calcium fluoride. The second focus lens 162 is preferably located between the second window 160 and the solar filter 164 and serves to reduce the diameter of the light that is received from the optical path measuring region 158 and passed to the detector 166.

The solar filter 164 preferably comprises long pass light filter centered around 2.0 m. The solar filter 164 is preferably located between the second focus lens 162 and the detector 166 and serves to prevent ambient light from being received by the detector. The solar filter 164 can be incorporated within the detector 166 or can comprise a separate element apart from the detector 166.

The detector 166 preferably comprises an infrared light detector such as a lead selenide detector. One suitable detector 166 is the Cal Sensors' lead selenide model B72S-18T. The detector 166 is preferably 1 mm by 1 mm in size and includes a two stage thermoelectric cooler. The detector is preferably longitudinally disposed 5 inches from the source 120.

The gas analyzer 100 preferably further comprises a scrubber 170 and a desiccant 180. The scrubber 170 preferably comprises a quantity of material for absorbing gas or vapor as described above. In a preferred embodiment, the scrubber 170 comprises a container with the material disposed therein that includes a permeable cover. The scrubber 170 is preferably disposed within the housing 150. Alternatively, the scrubber 170 can be located external to the housing 110 but can be coupled with the housing so that gas can flow between the housing 110 and the scrubber 170.

The desiccant 180 preferably comprises a quantity of material for absorbing vapor as described above. In a preferred embodiment, the desiccant 180 comprises a container with the material disposed therein that includes a permeable cover. for removing $H_2O$. The desiccant 180 is preferably disposed within the housing 110. Alternatively, the desiccant 180 can be located external to the housing 110 but can be coupled with the housing so that gas can flow between the housing 110 and the desiccant 180. In a preferred embodiment, the gas analyzer 110 further comprises a circulator for moving the gas within the housing 110 and increasing the flow of gas into the scrubber 170 and the desiccant 180. One such circulator can comprise a chopper wheel and a motor. The chopper wheel can be formed or shaped such that rotation of the chopper wheel causes air or other gases to be circulated.

While the embodiments described above are provide examples of analyzers suitable for measuring $CO_2$ and $H_2O$, the analyzers can be used to measure other gases such as nitrogen oxides, carbon monoxide, methane, and other such gases.

The disclosed gas analyzer provides for the effective measurement of gases contained within a sample through the use of multiple reference filters. In addition, the gas analyzer provides for the effective scrubbing of gases within the analyzer's housing through the use of gas channels, which join different parts of the housing.

It is to be understood that a wide range of changes and modifications to the embodiments described above will be apparent to those skilled in the art and are contemplated. It is therefore intended that the foregoing detailed description be regarded as illustrative rather than limiting, and that it be understood that it is the following claims, including all equivalents, that are intended to define the spirit and scope of the invention.

I claim:

1. A gas analyzer comprising:
   a housing comprising:
      a first housing section;
      a second housing section longitudinally disposed from the first housing section to form an open air optical path measuring region between the first and second housing sections; and
      a gas channel coupling the first housing section with the second housing section;
   a source disposed within the housing; and
   a detector disposed within the housing,
   wherein the gas channel enables purged gas to flow between the first and second housing sections.

2. The invention of claim 1, wherein the source and the detector are approximately 5 inches apart.

3. The invention of claim 1, further comprising a second gas channel coupling the first housing section with the second housing section.

4. The invention of claim 1, further comprising a scrubber coupled with the housing.

5. The invention of claim 1, further comprising a scrubber located within the housing.

6. The invention of claim 1, further comprising a desiccant coupled with the housing.

7. The invention of claim 1, further comprising a desiccant located within the housing.

8. A gas analyzer comprising:
   a housing comprising:
      a first housing section;
      a second housing section longitudinally disposed from the first housing section to form an open air optical path measuring region between the first and second housing sections; and
      a plurality of gas channels coupling the first housing section with the second housing section;
   a source disposed within the first housing section;
   a scrubber disposed within the first housing section;
   a desiccant disposed within the first housing section;
   a filter member disposed within the first housing section, the filter member comprising first and second sample filters and first and second reference filters; and
   a detector disposed within the second housing section, the detector being optically coupled with the source to create an open air optical path,
   wherein the gas channels enable purged gas to flow between the first and second housing sections,
   wherein the filter member is movably disposed to intermittently introduce the first and second sample filters and the first and second reference filters in an optical path between the source and the detector.

9. The invention of claim 8, wherein the first sample filter comprises a $CO_2$ filter.

10. The invention of claim 8, wherein the second sample filter comprises a $H_2O$ filter.

11. The invention of claim 8, wherein the first sample filter comprises a band pass filter centered around 4.25 $\mu$m.

12. The invention of claim 8, wherein the second sample filter comprises a band pass filter centered around 2.59 $\mu$m.

13. The invention of claim 8, wherein the first reference filter comprises a band pass filter centered around 4.0 $\mu$m.

14. The invention of claim 8, wherein the second reference filter comprises a band pass filter centered around 2.3 $\mu$m.

* * * * *

UNITED STATES PATENT AND TRADEMARK OFFICE
CERTIFICATE OF CORRECTION

PATENT NO.   : 6,317,212 B1
DATED        : November 13, 2001
INVENTOR(S)  : Robert D. Eckles It is certified that error appears in the above-identified patent and that said Letters Patent is hereby corrected as shown below:

Column 2,
Lines 9-10, delete "*Meterology*24" and substitute -- *Meterology* 24 -- in its place.

Signed and Sealed this

Nineteenth Day of November, 2002

*Attest:*

JAMES E. ROGAN
*Director of the United States Patent and Trademark Office*

*Attesting Officer*